United States Patent
Tinger

(10) Patent No.: US 11,332,422 B2
(45) Date of Patent: May 17, 2022

(54) SYSTEMS AND METHODS FOR DEEP CRYSTALLIZATION OF XYLENE STREAMS

(71) Applicant: ExxonMobil Chemical Patents Inc., Baytown, TX (US)

(72) Inventor: Robert G. Tinger, Friendswood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 5 days.

(21) Appl. No.: 16/605,378

(22) PCT Filed: Apr. 17, 2018

(86) PCT No.: PCT/US2018/027930
§ 371 (c)(1),
(2) Date: Oct. 15, 2019

(87) PCT Pub. No.: WO2018/217327
PCT Pub. Date: Nov. 29, 2018

(65) Prior Publication Data
US 2020/0048169 A1 Feb. 13, 2020

Related U.S. Application Data

(60) Provisional application No. 62/509,861, filed on May 23, 2017.

(51) Int. Cl.
C07C 7/14 (2006.01)
C07C 5/27 (2006.01)
C07C 7/00 (2006.01)

(52) U.S. Cl.
CPC ............... *C07C 7/14* (2013.01); *C07C 5/2732* (2013.01); *C07C 7/005* (2013.01)

(58) Field of Classification Search
CPC ........................................................ C07C 7/14
See application file for complete search history.

(56) References Cited

U.S. PATENT DOCUMENTS 3,662,013 A    5/1972  Machell et al.
3,963,795 A *  6/1976  Wood ....................... C07C 7/005
                                                    585/816
(Continued)

OTHER PUBLICATIONS

Lima, Ricardo M. et al. "Optimal synthesis of p_xylene separation processes based on crystallization technology," American Institute of Chemical Engineers AIChE Journal, 2009, vol. 55, No. 2, pp. 354-373 See abstract; p. 356, right column; and figure 2.
(Continued)

*Primary Examiner* — Philip Y Louie
*Assistant Examiner* — Alyssa L Cepluch

(57) ABSTRACT

Methods for the production of para-xylene include flowing a xylenes-containing stream comprising PX, meta-xylene (MX), and ortho-xylene (OX), to a first crystallization stage. In addition, the methods include lowering a temperature of the xylenes-containing stream to below the eutectic point of the xylenes-containing stream within the first crystallization stage to crystallize at least some of the PX and at least some of one of both of the MX and the OX within the xylenes-containing stream. Further, the methods include separating the xylenes-containing stream into a first crystallization effluent stream and a first filtrate stream.

19 Claims, 4 Drawing Sheets

(56) References Cited

U.S. PATENT DOCUMENTS

2008/0249345 A1* 10/2008 Kinn .................. C07C 6/123
  585/470
2012/0108868 A1   5/2012 Pilliod et al.
2012/0234516 A1   9/2012 Jin et al.
2015/0299071 A1* 10/2015 Ou .................... C10G 45/58
  585/300

OTHER PUBLICATIONS

Shiau, Lie-Ding et al., "Separation of p_xylene from the multicomponent xylene system by stripping crystallization," American Institute of Chemical Engineers Aiche Journal, 2008, vol. 54, No. 1, pp. 337-342 See p. 337, left column; and tables 3-11.
Shiau, Lie-Ding et al.,"Separation and Purification of p-Xylene from the Mixture of m-Xylene and p-Xylene by Distillative Freezing," Industrial and Engineering Chemistry Research, 2005, vol. 44, No. 7, pp. 2258-2265 See abstract and conclusions.

* cited by examiner

SYSTEMS AND METHODS FOR DEEP CRYSTALLIZATION OF XYLENE STREAMS

CROSS-REFERENCE OF RELATED APPLICATIONS

This application is a National Phase Application claiming priority to PCT Application Serial No. PCT/US2018/027930 filed Apr. 17, 2018, which claims the benefit of and priority to U.S. Provisional Application Ser. No. 62/509,861, filed May 23, 2017, and entitled, "Systems and Method for Deep Crystallization of Xylene Streams," which is incorporated herein by, reference in its entirety.

TECHNICAL FIELD

This disclosure generally relates to the production of para-xylene. More particularly, this disclosure relates to the production of para-xylene utilizing crystallization techniques.

BACKGROUND

Crystallization processes are used to separate paraxylene (PX) from a $C_8$ aromatic starting material which contains ethylbenzene (EB), as well as the three xylene isomers (i.e., PX, metaxylene (MX), and orthoxylene (OX)). Use is made in these processes of the fact that the freezing points of the individual $C_8$ isomers have significant temperature differences. Specifically, PX has a freezing point of 13.3° C., MX has a freezing point of −47.9° C., and OX has a freezing point of −25.2° C. However, conventional crystallization methods require great expense to make PX with a purity of over 99.5 wt. % based on the total weight of the product stream.

Crystallization processes to recover PX from a mixture of $C_8$ aromatics requires cooling the equilibrium feed mixture, which may be produced from a previous process (e.g., from reformate or xylene isomerization processes). Because the freezing point of PX is much higher than that of the other $C_8$ aromatics, PX is readily separated in the crystallizer after refrigeration of the stream. In many PX crystallization processes, the feed may include, among other components, mixed xylenes (i.e., PX, OX, MX at equilibrium concentration). Typically, an equilibrium concentration of xylenes comprises approximately 24 wt. % PX, approximately 26 wt. % OX, and approximately 50 wt. % MX, where the wt. % above are listed based on the total weight or xylenes within the stream. In order to crystallize and isolate at least some portion of the PX from solution, crystallization processes include a step of cooling the feed below the freezing point of PX (i.e., below approximately 13.3° C.). Conventional crystallization processes operate in the manner described in U.S. Pat. No. 3,662,013.

In conventional crystallization processes, the maximum theoretical PX recovery is fixed by the temperature of the coldest crystallizer in the crystallization unit. That temperature is limited by eutectic temperature of the stream subject to the crystallization process (referred to herein as the "eutectic temperature," or the "eutectic point"). Generally speaking, the eutectic point refers to the temperature at which multiple components in a given mixture co-crystallize. Specially, as used herein, the eutectic temperature of a xylenes-containing stream refers to the temperature at which at least 1 wt. % of MX or OX co-crystallizes with PX. For mixed xylenes at equilibrium concentrations, the eutectic temperature is typically equal to approximately −90° F. (−68° C.). It should be appreciated that one having ordinary skill would fully understand how to calculate or otherwise determine the eutectic temperature for a given feed stream. As a result, given an equilibrium mixture of xylenes in the crystallizer feed, the coldest crystallizer in a conventional crystallization process is therefore typically cooled to about 5° F.-10° F. (~3°-5° C.) above the eutectic temperature (e.g., typically to around −80° F. to around −90° F. or −62° C. to −68° C., respectively) to maximize PX recovery, and avoid co-crystallizing the other xylene isomers (e.g., MX, OX).

BRIEF SUMMARY

The embodiments disclosed herein include systems and processes for producing PX from a xylenes-containing stream by crystallizing the xylenes-containing stream below the eutectic point of the xylenes-containing stream. As a result, in the disclosed embodiments, at least some of the other xylene isomers (e.g., MX and/or OX) co-crystalize with PX in the crystallization process, and must be isolated and separated out of the resulting crystallization effluent. In at least some embodiments, the co-crystallized MX and OX is separated and removed from the PX product by additional crystallization, separation, and/or isomerization steps. In addition, in at least some embodiments, the resulting PX-rich stream from the sub-eutectic crystallization is routed to subsequent crystallization and separation steps to further purify the resulting PX product stream.

At least some specific embodiments disclosed herein are directed to a process for producing PX. In an embodiment, the process includes flowing a xylenes-containing stream comprising PX, MX, and OX, to a first crystallization stage. In addition, the process includes lowering a temperature of the xylenes-containing stream to 10° F. or more below the eutectic point of the xylenes-containing stream within the first crystallization stage to crystallize at least some of the PX and at least some of one of both of the MX and the OX within the xylenes-containing stream. Further, the process includes separating the xylenes-containing stream into a first crystallization effluent stream and a first filtrate stream.

Other specific embodiments of a process for producing PX disclosed herein include flowing a feed stream to a separation tower, and separating a xylenes-containing stream from the feed stream within the separation tower. The xylenes-containing stream comprises PX, MX, and OX. In addition, the process includes flowing the xylenes-containing stream to a first crystallization stage, lowering a temperature of the xylenes-containing stream to −100° F. (−73.33° C.) or lower within the first crystallization stage to crystallize at least some of the PX and at least some of one of both of the MX and the OX within the xylenes-containing stream, and separating the xylenes-containing stream into a first crystallization effluent stream and a first filtrate stream. Further, the process includes flowing the first crystallization stage effluent stream to a second crystallization stage, changing the temperature of the first crystallization stage effluent stream within the second crystallization stage to a first point above the freezing to point of MX and the freezing point of OX, but below the freezing point of PX, and separating the first crystallization stage effluent stream into a second crystallization stage effluent stream and a second filtrate stream. Still further, the process includes flowing the second filtrate stream to a first liquid phase isomerization unit to produce a first isomerized stream, and recycling the first isomerized stream to at least one of the first crystallization stage, or the second crystallization stage.

DETAILED DESCRIPTION

Figure 1:
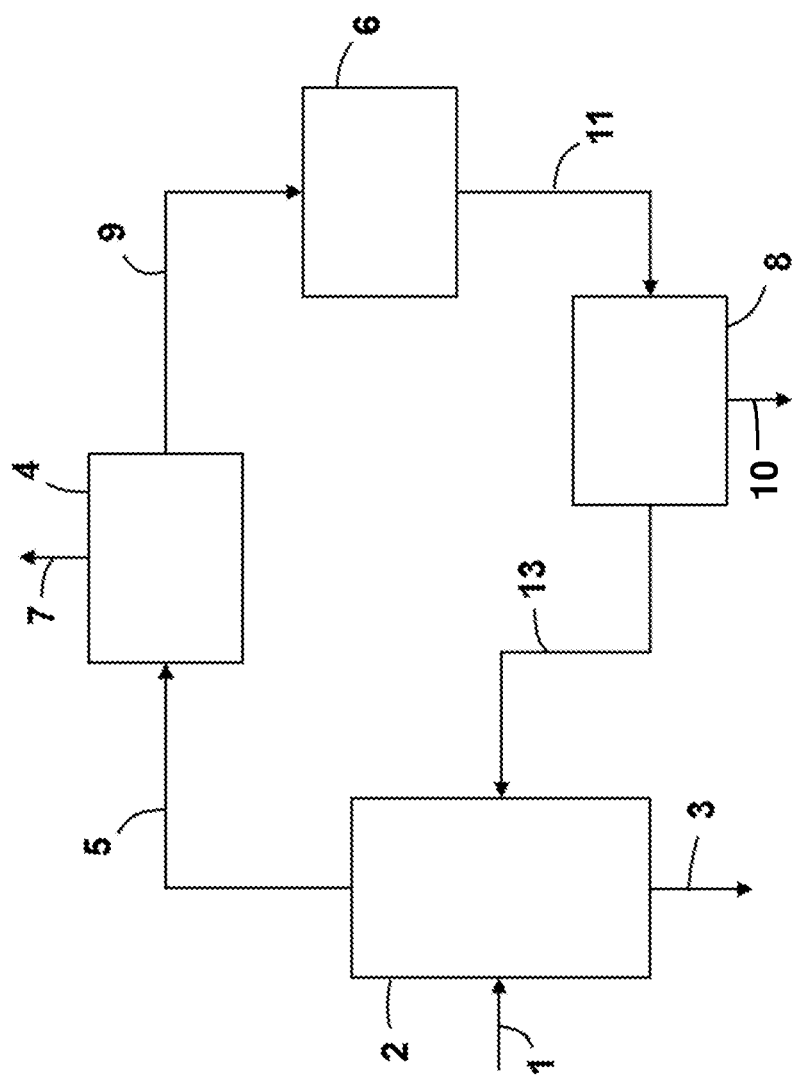
FIG. 1 is a flow chart of a conventional xylene production loop.

The following discussion is directed to various embodiments. However, it should be appreciated that the embodiments disclosed herein have broad application, and that the discussion of any embodiment is meant only to be exemplary of that embodiment, and not intended to suggest that the scope of the disclosure, including the claims, is limited to that embodiment. In the drawings, certain features and components herein may be shown exaggerated in scale or in somewhat schematic form and some details of conventional elements may not be shown in interest of clarity and conciseness. All documents described herein are incorporated by reference, including any priority documents and/or testing procedures, to the extent they are not inconsistent with this text. When numerical lower limits and numerical upper limits are listed herein, ranges from any lower limit to any upper limit are contemplated.

As used herein, the term "$C_n$" hydrocarbon wherein n is a positive integer, e.g., 1, 2, 3, 4, or 5, means a hydrocarbon having n number of carbon atom(s) per molecule. In addition, as used herein the term "$C_{n+}$" hydrocarbon wherein n is a positive integer, e.g., 1, 2, 3, 4, or 5, means hydrocarbon having at least n number of carbon atom(s) per molecule. Further, the term "$C_{n-}$" hydrocarbon wherein n is a positive integer, e.g., 1, 2, 3, 4, or 5, means a hydrocarbon having no more than n number of carbon atom(s) per molecule. As used herein the term "aromatics" means hydrocarbon molecules containing at least one aromatic core. As used herein the term "hydrocarbon" encompasses mixtures of hydrocarbon, including those having different values of n. As used herein and unless otherwise specified, the terms "approximately," "substantially," "about," mean+/−10%. As used herein, a stream that is said to be "rich" in any one of the xylenes isomers (i.e., PX, MX, OX) means a stream that includes more than equilibrium concentrations of that xylene isomer. Thus, as an example, a stream containing more than ~24 wt. % para-xylene based on the total weight of xylenes contained therein may be referred to as a para-xylene rich stream since it contains more than the equilibrium concentration of para-xylene of ~24 wt. % based on the total weight of xylenes contained therein. As used herein, the term "rich" when used in phrases such as "X-rich" or "rich in X" means, with respect to an outgoing stream obtained from a device, that the stream comprises material X at a concentration higher than in the feed material fed to the same device from which the stream is derived.

Referring now to FIG. 1, a conventional process for producing a PX rich stream is shown. In this process, a de-toluenized feed 1 is provided to a fractionation tower 2 which emits an overhead $C_8$ aromatics stream 5 and a bottoms $C_{9+}$ aromatics stream 3. The overhead $C_8$ aromatics stream 5 is fed to a PX recovery unit 4 which is configured to separate and produce a PX-rich stream 7 and a PX depleted stream 9. PX recovery unit 4 may utilize any suitable PX selective purification process, such as, for example, selective adsorption or crystallization process. In some instances, PX recovery unit 4 may be configured to produce a PX rich stream 7 having a PX content of 99.7 wt. % based on the total weight of xylenes within stream 7. The PX depleted stream 9 is sent to a xylene isomerization unit 6 to return the xylenes within stream 9 back to equilibrium concentrations (i.e., ~24 wt. % PX, ~26 wt. % OX, and ~50 wt. % MX). In addition, isomerization unit 6 may convert any EB within stream 9 to either to benzene and ethane or to PX, and/or convert non-aromatic co-boiling hydrocarbons to gas. Isomerization unit 6 products an isomerized stream 11 that is routed to a detoluenization tower 8, which separates light by-produces from xylene isomerization unit 6 (e.g., $C_5$ hydrocarbons, benzene, toluene, etc.) from the relatively heavier xylenes, EB, and $C_{9+}$ aromatic hydrocarbons. The lighter by-products are produced from detoluenization tower 8 at line 10, and the xylenes, EB, and $C_{9+}$ aromatic hydrocarbons are emitted from tower 8 via line 13 which is recycled back to fractionation tower 2.

The circulation between units 2, 4, 6, 8, via lines 5, 9, 11, and 13 defines a xylenes loop. The efficiency of the xylenes loop is defined by the number of times xylenes must circulate the loop to obtain the desired level of PX purity (e.g., approximately 99.7 wt. % based on the total amount of xylenes). The number of times xylenes are circulated around the xylenes loop is also referred to herein as the xylenes loop traffic. Due to the energy required to operate the xylenes loop, as the xylenes loop traffic increases, the relative energy requirements and costs for operating the xylene production process also increases. When a selective adsorption technique is used in the PX recovery unit 4, the xylene loop traffic is typically around 3 to 4. Conversely, when a conventional crystallization technique is used within PX recovery unit 4, the xylene loop traffic can be 5 or more.

One option for achieving higher PX recovery rates, and thus, lower xylenes loop traffic numbers for crystallization techniques would be to lower the temperature of crystallization to crystallize a larger percentage of the PX within the feed stream. However, as previously described, PX crystallization processes typically specifically avoid cooling the process stream to below the eutectic point in order to prevent co-crystallizing MX and/or OX which contaminates the product PX stream. Accordingly, embodiments disclosed herein include systems and methods providing PX crystallization processes that cool the process flow to a point below the eutectic point while avoiding the ultimate production of MX and/or OX along with the product PX stream. Without being limited to this or any other theory, by crystallizing the xylene feed into a crystallization process below the eutectic point, a higher percentage of the PX within the feed stream may be separated with a single pass through the crystallization unit(s), which thereby reduces the loop traffic and increases the efficiency for such a crystallization process.

Figure 2:
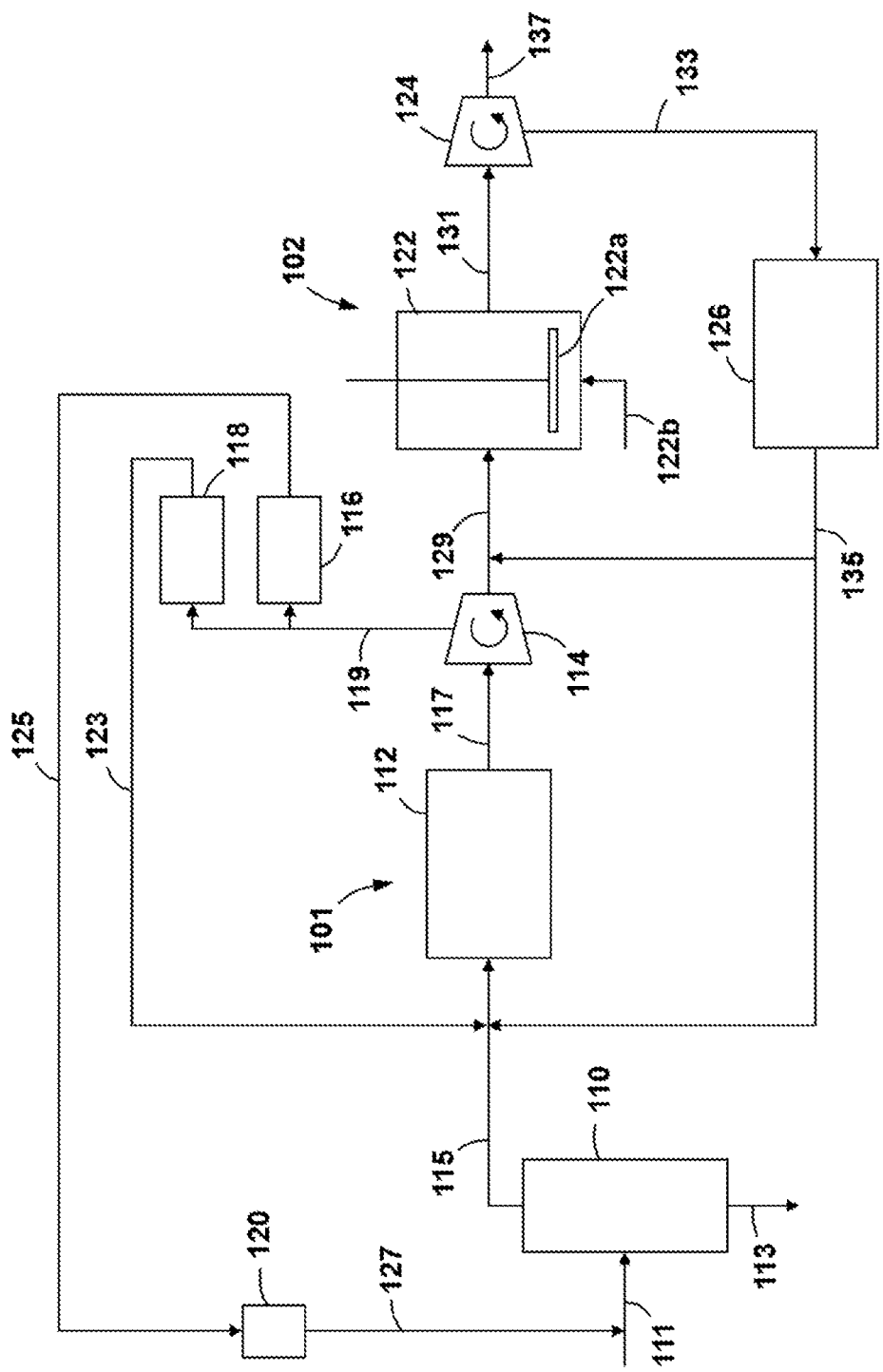
FIG. 2 is a flow chart of a process for producing a PX stream according to at least some embodiments disclosed herein.

Referring now to FIG. 2, an embodiment of a PX production process and system that includes sub-eutectic point crystallization in accordance with at least some of the embodiments disclosed herein is shown. In FIG. 2, a feed stream 111 is routed to a xylenes separation tower 110. Feed stream 111 may be derived from a variety of sources, such as, for example, from $C_{8+}$ reformate, $C_{8+}$ selective or unselective toluene disproportionation product, $C_{8+}$ transalkylation product, alkylation product (e.g., such as from benzene and/or toluene alkylation). Thus, it should be appreciated that any stream or combination of streams that contain xylenes may be utilized as feed stream 111. As a result, feed stream 111 may be referred to herein as a "xylene-containing" stream 111. Xylenes separation tower 110, which may comprise one or more distillation columns and/or other separation devices, receives feed stream 111 and outputs a bottoms stream 113 comprising $C_{9+}$ hydrocarbons (including aromatics) compounds, and an overhead stream 115 comprising $C_{8-}$ hydrocarbons (including $C_8$ aromatic compounds). Optionally (and not specifically shown in FIG. 1), bottoms stream 113 may be sent to one or more processing units, such as, for example, a transalkylation process unit.

In at least some embodiments, the xylenes within overhead stream 115 may comprise PX, MX, OX, and EB. In addition, in at least some of these embodiment, the PX, MX, and OX within overhead stream 115 are present in equilibrium conditions. Overhead stream 115 is routed from xylenes separation tower 110 to a first crystallization stage 101 where the temperature of the overhead stream 115 is reduced below the eutectic point, which as previously described above is the temperature at which at least 1 wt. % of OX or MX co-freezes or co-crystallizes with PX. In particular, in this embodiment the first crystallization stage 101 comprises a deep crystallization unit 112 and a centrifuge 114. During operations, the temperature of overhead stream 115 is reduced below the eutectic point for the stream composition in overhead stream 115 in first crystallization stage 101. For example, in some embodiments, the temperature of overhead stream 115 is reduced at least 1 degree (e.g., Fahrenheit, Celsius, Kelvin, etc.) below the eutectic point first crystallization stage 101. In other embodiments, the temperature of overhead stream 115 is reduced at least 3-5, 10, 20, 50, 100 or more degrees (e.g., Fahrenheit, Celsius, Kelvin, etc.) below the eutectic point in first crystallization stage 101. In at least some embodiments, the temperature of overhead stream 115 is reduced to or close to the point where ethylbenzene (EB) at least partially co-freezes with the xylenes within stream 115 (e.g., approximately −140° F.). In still other embodiments, the temperature of overhead stream 115 is reduced approximately −100° F. (~−73.33° C.) in first crystallization stage 101. In other words, within deep crystallization unit 112 the temperature of overhead stream 115 is reduced well below the eutectic point of approximately −90° F. (−68° C.). As a result, MX and/or OX will at least partially co-crystallize with PX within deep crystallization unit 112. However, in at least some embodiments, any EB within the deep crystallization unit 112 will remain substantially un-crystallized due to a much lower freezing point of −140° F. (−95° C.). The effluent of deep crystallization unit 112 is routed via line 117 to centrifuge 114 (or other suitable separation unit), which separates the crystallized and un-crystallized portions of the stream in line 117 from one another. In particular, centrifuge 114 produces a first crystallization stage effluent stream 129 comprising a majority of crystallized PX, MX, and OX, and a PX-depleted filtrate stream 119. In some embodiments, first crystallization stage effluent stream 129 may comprise 50 wt. % PX, and therefore may be referred to herein as a PX rich stream. In addition, in some embodiments, filtrate stream 119 may comprise about 6 to 7 wt. % PX or less (e.g., 3 wt. % PX) based on the total weight of xylenes in the stream.

Upon being emitted from centrifuge 114, PX-depleted filtrate stream 119 is provided to a vapor phase isomerization unit 116 and/or optionally a liquid phase isomerization unit 118 to return any xylenes within filtrate stream 119 back to equilibrium concentration levels. In addition, flow to vapor phase isomerization unit 116 and/or liquid phase isomerization unit 118 also may work to convert at least some of the EB within filtrate stream 119 into benzene and/or PX. However, as would be appreciated by one having ordinary skill in the art, a greater percentage of the EB within filtrate stream 119 flowing into vapor phase isomerization unit 116 will be processed into benzene and/or PX than within the filtrate stream 119 flowing to liquid phase isomerization unit 118.

Vapor phase isomerization unit 116 and liquid phase isomerization unit 118 may use one or more of a variety of catalysts that are per se well-known in the art. In this regard, see for example, U.S. Pat. Nos. 8,697,929; 8,273,934; 7,932,426; 6,180,550; 6,448,459; 6,872,866; 7,244,409; 7,371,913; 7,495,137; 7,592,499, and U.S. Publication No. 2012/0108868 A1, the contents of each being incorporated herein by reference.

The operating conditions of vapor phase isomerization unit are configured to maintain the filtrate stream 119 in a substantially vapor phase. For example, in some embodiments, most (e.g., more than 50 wt. %), all (100 wt. %) or substantially all (90-99 wt. %) of filtrate stream 119 is maintained in the vapor phase within vapor phase isomerization unit 116. In some embodiments, the operating conditions for vapor phase isomerization unit 116 include a temperature of about 300 to about 500° C., a pressure of about 5 Bar (0.5 MPa) to about 500 Bar (50 MPa), and a weight hourly space velocity of about 4 to about 20 $hr^{-1}$.

By contrast, the operating conditions of liquid phase isomerization unit 118 are configured to maintain the filtrate stream 119 in a substantially liquid phase. For example, in some embodiments, most (e.g., more than 50 wt. %), all (100 wt. %) or substantially all (e.g., 90-99 wt. %) of filtrate stream 119 is maintained in the liquid phase within liquid phase isomerization unit 118. In some embodiments, the operating conditions for liquid phase isomerization unit 118 include a temperature of about 180 to about 280° C., a pressure of about 10 Bar (1 MPa) to about 20 Bar (2 MPa), and a weight hourly space velocity of about 1 to about 20 $hr^{-1}$.

Vapor phase isomerization unit 116 produces a first isomerized stream 125 that is flowed to a detoluenization tower 120 which removes at least a portion of any $C_{7-}$ hydrocarbons (e.g., $C_{7-}$ aromatics) from stream 125, and thereafter emits a detoluenized stream 127 that is merged with feed stream 111 upstream of xylenes separation tower 110. In other embodiments, no detoluenization tower 120 is included and isomerized stream 125 is merged directly with feed stream 111 upstream of xylenes separation tower 110. Liquid phase isomerization unit 118 produces a second isomerized stream 123 that is merged with overhead stream 115 upstream of deep crystallization unit 112.

It should be appreciated that in some embodiments, liquid phase isomerization unit 118 is not included and all of the filtrate stream 119 from centrifuge 114 is routed to vapor phase isomerization unit 116. Likewise, in still other embodiments, no vapor phase isomerization unit 116 is included and all of the filtrate stream 119 from centrifuge 114 is routed to liquid phase isomerization unit 118. In still further embodiments, both vapor phase isomerization unit 116 and liquid phase isomerization unit 118 are included and the filtrate stream 119 is split (e.g. in any ratio) and fed to both units 116, 118, such as is shown in the embodiment of FIG. 2.

Referring still to FIG. 2, first crystallization stage effluent stream 129 is routed to a second crystallization stage 102, which in this embodiment comprises a recovery unit 122 and a centrifuge 124. In this embodiment, recovery unit 122 is a re-slurry unit including one or more agitators 122a and a warm input stream 122b comprising any suitable stream that is warmer than first crystallization stage effluent 129. For example, in some embodiments, warm input stream 122b is between about −30° F. (−34° C.) to about −80° F. (−62° C.), and may comprise filtrate streams 133, 143, and/or 155 (discussed below), or any other internal or external stream. During operations, the first crystallization stage effluent stream 129 is routed to recovery unit 122 in second crystallization stage 102 where it is mixed with the warm input stream 122b (e.g., via agitator 122a) so that the temperature of first crystallization stage effluent is raised above the eutectic point (e.g., −90° F. or −67.8° C.). In at least some embodiments, first crystallization stage effluent stream 129 is raised within recovery unit 122 to a point above the melting points of MX (i.e., −47.9° C. or −54.2° F.) and/or OX (−25.2° C. or −13.4° F.) but below the melting point of PX (i.e., 13.3° C. or 56° F.). In other embodiments, the operating temperature of recovery unit 122 is set to be approximately 4° F. to 10° F. above the eutectic point of the first crystallization stage effluent stream 129. For example, in some embodiments, the temperature of recovery unit 122 (i.e., the temperature of the materials flowing within recovery unit 122) is approximately −80° F. (−62.2° C.). As a result of the relatively higher temperature of recovery unit 122, a majority of the MX and OX crystals in first crystallization effluent stream 129 melt, but a majority of the PX crystals (which have a melting point of 55.8° F. or 13.2° C.) remain frozen in a crystallized form. An output stream 131 from recovery unit 122 is routed to another centrifuge 124, or other suitable separation device, which separates a second crystallization stage effluent stream 137 comprising crystallized PX, from a filtrate stream 133 comprising MX and OX. In some embodiments, filtrate stream 133 may comprise some PX. For example, in some embodiments, filtrate stream 133 comprises approximately 10 wt. % PX or less based on the total weight of xylenes in filtrate stream 133.

It should also be appreciated that in other embodiments, recovery unit 122 is to replaced with a heat exchanger that is configured to raise the temperature of first crystallization stage effluent stream 129 above the eutectic point (e.g., −80° F. or −62.2° C.). In still other embodiments, both a heat exchanger and recovery unit 122 are utilized to raise the temperature of first crystallization stage effluent stream 129 above the eutectic point as described above. In these embodiments the heat exchanger and recovery unit 122 may be placed in series, such that either recovery unit 122 is upstream of the heat exchanger or the heat exchanger is upstream of the recovery unit 122.

Filtrate stream 133 is routed to another liquid phase isomerization unit 126 which produces an isomerized stream 135 that includes xylenes at substantially equilibrium levels or amounts. In other words, liquid phase isomerization unit 126 converts the MX and OX rich filtrate stream into a stream (e.g., stream 135) that includes mixed xylenes at equilibrium concentrations (e.g., ~24 wt. % PX, ~24 wt. % OX, ~50 wt. % MX). In at least some embodiments, liquid phase isomerization unit 126 may be configured the same as liquid phase isomerization unit 118, previously described above. In addition, in at least some embodiments, filtrate stream 133 may be merged with filtrate stream 119 upstream of liquid phase isomerization unit 118 so that isomerization unit 126 is not included. Therefore, by placing liquid phase isomerization unit 126 downstream of recovery unit 122, excess MX and OX that was crystallized within deep crystallization unit 112 can be reduced and/or isomerized prior to recycling them back toward crystallization unit 112. As a result, crystallization unit 112 may be operated below the eutectic point, which facilitates the crystallization of a greater percentage of the PX within the process stream, all the while avoiding the additional buildup of MX and OX within the process.

As shown in FIG. 2, the isomerized stream 135 may be merged with one or more of first crystallization stage effluent stream 129 and overhead stream 115. For example, in some embodiments, isomerized stream 135 is split and merged with both overhead stream 115 and first crystallization stage effluent stream 129. In other embodiments, isomerized stream 135 is only merged with one of the overhead stream 115 and first crystallization stage effluent stream 129. The choice of routing for isomerized stream 135 is based at least in part on the amount of EB in isomerized stream 135. Specifically, in some embodiments, if the EB content in isomerized stream 135 is high (e.g., 10 wt. % or more), then isomerized stream 135 is merged with overhead stream 115. Conversely, if the EB content in isomerized stream 135 is low (e.g., 5 wt. % or less), then isomerized stream 135 is merged with first crystallization stage effluent stream 129 as allowed by the refrigeration limit in the deep crystallization unit 112.

Figure 3:
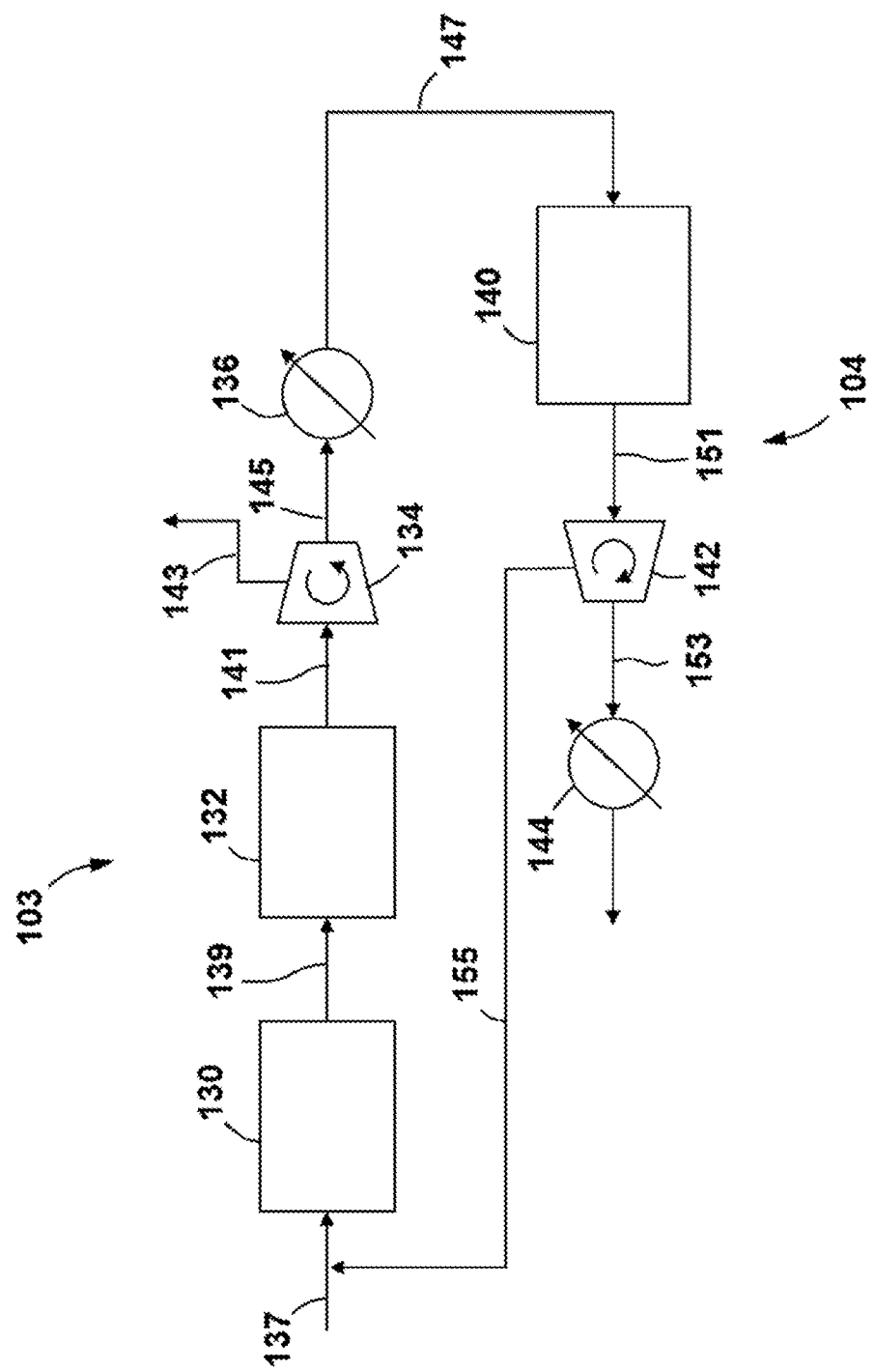
FIG. 3 is a flow chart of a purification process for use in conjunction with the process of FIG. 2 in accordance with at least some embodiments disclosed herein.

Referring now to FIG. 3, at least a portion (and in some embodiments all) of second crystallization stage effluent stream 137 resulting from the process of FIG. 2 is routed to a purification process. FIG. 3 shows an example of a purification process for use in at least some embodiments disclosed herein.

Initially, second crystallization stage effluent stream 137, which may comprise approximately 90 wt. % PX or more based on the total weight of the xylenes in stream 137, is flowed to a third crystallization stage 103, which comprises pair of crystallization units 130, 132 and a centrifuge 134. In other embodiments, more or less than two crystallization units 130, 132 may be utilized in third crystallization stage 103. Crystallization units 130, 132 are arranged in series and are configured to operate such that crystallization unit 130 operates at a lower temperature than crystallization unit 132. In addition, both crystallizer units 130, 132 operate at a higher temperature than recovery unit 122 (see FIG. 2). Specifically, crystallization units 130, 132 are configured to raise the temperature of second crystallization stage effluent stream 137 to a point above the melting points of MX and OX (approximately −47.9° C. and −25.2° C., respectively) but below the melting point of PX (approximately 13.3° C.). In this embodiment, crystallization unit 130 operates at approximately −20° F. to −10° F. (i.e., about −29° C. to −23° C.) and crystallization unit 132 operates at approximately −10° F. to 25° F. (i.e., about −23° C. to −4° C.). In at least some embodiments, crystallization units 130, 132 utilize propane as a refrigerant.

The output from crystallizer unit 130 is routed to crystallizer unit 132 via line 139, and the output from crystallizer unit 132 is flowed to a centrifuge 134 via line 141. Centrifuge 134 separates the effluent in line 141 into a filtrate stream 143 which may comprise 40 wt. % PX as well as other compounds (e.g., approximately 0 to 60 wt. % MX, approximately 0 to 60 wt. % OX, etc.), and a third crystallization stage effluent stream 145 comprising crystallized PX. In some embodiments, the third crystallization stage effluent stream 145 may comprise approximately at least 95 wt. % PX based on the total weight of xylenes in effluent stream 145. The third crystallization stage effluent stream 145 is optionally flowed to a heat exchanger 136 which raises the temperature of stream 145 to 30°-55° F. While not specifically shown, it should be appreciated that filtrate stream 143 may be recycled to first crystallization stage 101 and/or second crystallization stage 102 (see FIG. 2).

Heat exchanger 136 emits a warmed stream via line 147 to a fourth crystallization stage 104, which comprises a crystallizer unit 140 and a centrifuge 142. Crystallizer unit 140 operates at a higher temperature than both crystallizer units 130, 132. Specifically, in this embodiment, crystallizer unit 140 operates at around 25° F. to 55° F. (−4° C. to 13° C.), which again is below the melting point of PX (approximately 13.3° C. or 56° F.) but is above the melting to points of other xylene isomers MX and OX (approximately −47.9° C. and −25.2° C., respectively). Therefore, within crystallizer unit 140, at least a majority of the PX remains crystalized, and at least a majority of the MX and OX transition to their liquid phases. Output from crystallizer unit 140 is passed to centrifuge 142 via line 151, which then separates effluent 151 into a filtrate stream 155 and a fourth crystallization stage effluent stream or PX product stream 153. In some embodiments, filtrate stream 155 may comprise approximately 75 to 95 wt. % PX and purified product stream 153 may comprise approximately 99.7 wt. % PX. Filtrate stream 155 is recycled and merged with second crystallization effluent stream 137 upstream of crystallizer units 130, 132, and PX product stream 153 is warmed in a heat exchanger 144 prior to being emitted from the process. In some embodiments heat exchanger 144 warms PX product stream 153 to at least the melting temperature of PX (i.e., approximately 56° F.). In other embodiment, heat exchanger 144 warms PX product stream 153 to at least 10° F. or more above the melting temperature of PX. In other embodiments, filtrate stream 155 may be recycled back to first crystallization stage and/or second crystallization stage either alternatively or additionally to recycling filtrate stream 155 to third crystallization stage as shown in FIG. 3. In addition, in other embodiments, warmed product stream 153 (i.e., product stream 153 downstream of heat exchanger 144) may be provided back to crystallizer unit 140 as a warm stream (e.g., in a manner similar to that shown above for warm stream 122b in recovery unit 122 in FIG. 2).

As a result of the embodiments disclosed herein, a xylene-containing feed stream is subject to a crystallization process whereby the temperature of the feed stream is reduced below the eutectic point for the xylene isomers (i.e., PX, OX, MX). Without being limited to this or any other theory, reducing the temperature of the process flow well below the eutectic point allows a greater percentage of the PX present within the feed stream to be crystallized and therefore separated out of the feed stream. In addition, the embodiments disclosed herein also address and therefore avoid the buildup of MX and OX within the product streams and/or recycle streams, so that contamination of the PX produced from the process is limited if not avoided altogether.

It should be appreciated that any suitable crystallizer technology, unit, apparatus, and/or system may be used for crystallizers 112, 122, 126, 130, 132, 140, such as for example, direct contact cooling, indirect contact cooling, centrifuge or filtration for solid/liquid separation (wherein either centrifuge or filters may be used), centrifuge wash, intervening melt stages, or combinations thereof. Each of these crystallization technologies may be configured as described in U.S. Pat. No. 8,252,967, the contents of which are incorporated herein by reference.

Particular reference will now be made to the following non-limiting example.

Figure 4:
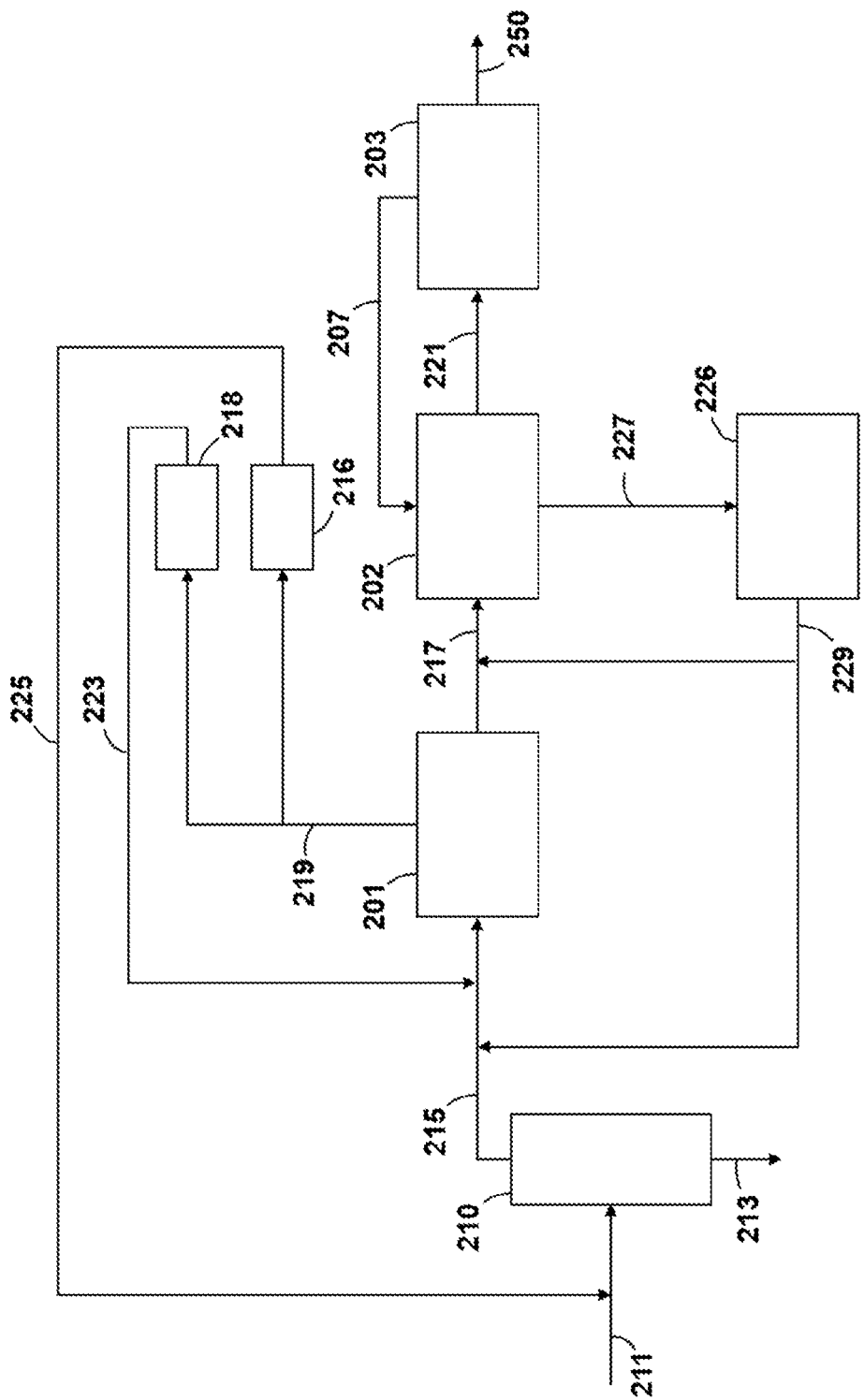
FIG. 4 is a flow chart of a process for producing a PX stream according to at least some embodiments disclosed herein.

FIG. 4 shows an embodiment of a process and system for producing a PX stream in accordance with at least some embodiments disclosed herein. The embodiment of FIG. 4 utilized to calculate the performance and efficiency of a deep crystallization process as described herein. Specifically, FIG. 4 shows a feed stream 211, which includes at least some $C_8$ aromatic hydrocarbons therein (e.g., PX, MX, OX, EB, etc.), that is routed to a separation unit 210, where an overhead stream 215 comprising $C_{8-}$ hydrocarbons (including $C_{8-}$ aromatic hydrocarbons) is separated from a bottoms stream 213 of $C_{9+}$ hydrocarbons. The overhead stream 215 is fed to a deep crystallization stage 201 (which may be the same or similar as first crystallization stage 101 in FIG. 2), where the temperature of stream 215 is lowered to below the eutectic point (e.g., such as previously described above).

A first raffinate stream 219, which comprises MX, OX, EB and possibly some PX is routed to a one or both of a vapor phase isomerization unit 216 and a liquid phase isomerization unit 218. Both isomerization units 216, 218 may be the same or similar to isomerization units 116, 118, respectively, previously described above and shown in FIG. 1. The liquid phase isomerization unit 218 may produce an isomerized stream 223 that is recycled back to overhead stream 215 upstream of deep crystallization stage 201, and vapor phase isomerization unit 216 may produce another isomerized stream 225 that is recycled back to feed stream 211 upstream of separation unit 210.

The first crystallization stage effluent stream 217, which comprises at least some crystallized PX along with at least some crystallized MX and/or OX is routed to a second crystallization stage 202 wherein the temperature of the effluent stream 217 is raised above the eutectic point but us maintained below the freezing point of PX (i.e., 56° F. or 13.3° C.). A second raffinate stream 227 is taken from second crystallization stage 202 that comprises MX, OX, and possibly some PX is routed to another liquid phase isomerization unit 226, which may be similar to isomerization unit 126 shown in FIG. 1 and discussed above. Liquid phase isomerization unit 226 produces another isomerized stream 229 that is routed to first effluent stream 217 upstream of second crystallization stage 202 and/or to overhead stream 215 upstream of deep crystallization stage 201.

Second crystallization stage effluent stream 221, which comprises a majority of PX, is routed to a third crystallization stage 203 where the temperature of the second crystallization stage effluent is raised again from the temperature in second crystallization stage 202 but is still maintained below the freezing point of PX (i.e., 56° F. or 13.3° C.). A third raffinate stream 207 is emitted from third crystallization stage 203 that is recycled back to second crystallization stage 202. Finally, third crystallization stage 203 emits an effluent stream 250 which is treated as a PX product stream, which has at least a 99.7 wt. % PX in some embodiments based on the total amount of xylenes within stream 250.

A calculation was run modeling the flow through the system shown in FIG. 4, the results of this calculation are shown below in Table 1. In the calculation, it was assumed that feed stream 211 included 100 kta of $C_8$ aromatic hydrocarbons with 14% EB and 86% mixed xylenes (i.e., PX, MX, OX) at equilibrium concentrations. In addition, it was assumed that PX product stream 250 comprised approximately 100 wt. % PX.

TABLE 1

| | |
|---|---|
| Feed Stream 211 (C8), kta | 100 |
| Feed stream 211 (xylenes), kta | 86 |
| Overhead stream 215, kta | 242 |
| PX product stream 250 (at 100 wt. % PX), kta | 82 |
| Isomerization Rate for Vapor Phase isomerization unit 216, kta | 124 |
| Isomerization Rate for Liquid Phase isomerization unit 218, kta | 334 |
| EB conversion rate for Vapor Phase Isomerization unit 216, % | 80 |
| Xylene Losses, % | 2.8 |
| Deep Crystallization Stage Rate, kta | 210 |
| Deep Crystallization Stage Temperature, ° F. | −100 |
| Second Crystallization Stage Rate, kta | 438 |
| Second Crystallization Stage Temperature, ° F. | −80 |
| Third Crystallization Stage Rate, kta | 102 |
| Third Crystallization Stage Temperature, ° F. | 35 |
| Ratio of Overhead stream 215 to Feed Stream 211 (wt/wt) | 2.4 |
| Ratio of Vapor Phase Isomerized stream 225 to Feed Stream 211 (wt/wt) | 1.2 |

In the calculation of Table 1 above, the ratio of the overhead stream 215 to the feed stream 211 represents the loop traffic of the embodiment of FIG. 4. Therefore, by utilizing deep crystallization processes according to the systems and processes disclosed herein, the loop traffic around the xylenes production loop (e.g., the loop defined between xylenes separation tower 110, crystallization unit 112, isomerization units 116 and/or 118, and detoluenization tower 120 in FIG. 2, or the loop defined by separation unit 210, crystallization stage 201, isomerization units 216, and/or 218 in FIG. 4) may be reduced. Specifically, in the embodiment of FIG. 4, the loop traffic may be as low as approximately 2.4. As a comparison, conventional PX production technologies (e.g., crystallization, adsorption, etc.) may have loop traffic numbers close to or greater than 4 (e.g., 3.9, 4.7, etc.). Thus, the energy efficiency of the embodiments disclosed herein may show an improvement over other PX production methods (e.g., such as PX selective adsorption processes and other PX crystallization processes).

While various embodiments have been disclosed herein, modifications thereof can be made without departing from the scope or teachings herein. In particular, many variations and modifications of the systems, apparatus, and processes described herein are possible and are within the scope of the disclosed subject matter. Accordingly, embodiments disclosed herein are exemplary only and are not limiting. As a result, the scope of protection is not limited to the embodiments described herein, but is only limited by the claims that follow, the scope of which shall include all equivalents of the subject matter of the claims. Unless expressly stated otherwise, the steps in a method claim may be performed in any order. The use of identifiers such as (a), (b), (c) before steps in a method claim is not intended to and does not specify a particular order to the steps. Rather the use of such identifiers are used to simplify subsequent reference to such steps. Finally, the use of the term "including" in both the description and the claims is used in an open ended fashion, and should be interpreted as meaning "including, but not limited to."

What is claimed is:

1. A process, comprising:
   (a) flowing a xylenes-containing stream comprising para-xylene (PX), meta-xylene (MX), and ortho-xylene (OX), to a first crystallization stage, without feeding a stream of a solvent immiscible to the xylenes-containing stream into the first crystallization stage;
   (b) lowering a temperature of the xylenes-containing stream to 10° F. or more below the eutectic point of the xylenes-containing stream within the first crystallization stage to crystallize at least some of the PX and at least some of one of both of the MX and the OX within the xylenes-containing stream;
   (c) separating the xylenes-containing stream into a first crystallization effluent stream and a first filtrate stream after (b);
   (j) flowing the first crystallization stage effluent stream to a second crystallization stage without feeding a stream of a solvent immiscible to first crystallization stage effluent into the second crystallization stage;
   (k) changing the temperature of the first crystallization stage effluent stream within the second crystallization stage to a first point above approximately −54.2° F. and below approximately 55.9° F.; and
   (l) separating the first crystallization stage effluent stream into a second crystallization stage effluent stream and a second filtrate stream after (k).

2. The process of claim 1, wherein the first filtrate stream comprises about 7 wt. % or less PX based on the total weight of xylenes within the first filtrate stream.

3. The process of claim 2, further comprising:
   (d) flowing at least a portion of the first filtrate stream to a first liquid phase isomerization unit to produce a first isomerized stream; and
   (e) recycling the first isomerized stream to the first crystallization stage.

4. The process of claim 3, further comprising:
   (f) flowing a feed stream to a separation tower before (a) to produce the xylenes-containing stream;
   (h) flowing at least a portion of the first filtrate stream to a vapor phase isomerization unit to produce a second isomerized stream; and
   (i) recycling the second isomerized stream to the separation tower.

5. The process of claim 4, further comprising separating a $C_{7-}$ hydrocarbon-containing stream from the second isomerized stream before (i).

6. The process of claim 5, wherein the second filtrate stream comprises about 10 wt. % PX or less based on the total weight of xylenes within the second filtrate stream, and wherein the second crystallization stage effluent stream comprises about 90 wt. % or more PX based on the total weight of xylenes within the second crystallization stage effluent stream.

7. The process of claim 6, further comprising:
   (m) flowing the second filtrate stream to a second liquid phase isomerization unit to produce a third isomerized stream; and
   (n) recycling the third isomerized stream to at least one of:
   the first crystallization stage; or
   the second crystallization stage.

8. The process of claim 7, further comprising:
   (o) flowing the second crystallization stage effluent stream to a third crystallization stage;
   (p) changing the temperature of the second crystallization stage effluent stream within the third crystallization stage to a second point that is above the first point and below approximately 55.9° F.; and (q) separating from the second crystallization stage effluent stream a third crystallization stage effluent stream and a third filtrate stream after (p).

9. The process of claim 8,
wherein the third crystallization stage comprises a first crystallizer unit and a second crystallization unit; and
wherein (p) further comprises:
(p1) changing the temperature of the second crystallization stage effluent stream within the first crystallizer unit to a third point that is above the first point and below the second point; and
(p2) changing the temperature of the second crystallization stage effluent stream within the second crystallizer unit to the second point after (p1).

10. The process of claim 9, further comprising:
(r) flowing the third crystallization stage effluent stream to a fourth crystallization stage;
(s) changing the temperature of the third crystallization stage effluent stream with the fourth crystallization stage to a fourth point that is above the second point and below approximately 55.9° F.;
(t) separating from the third crystallization stage effluent stream a PX product stream and a fourth filtrate stream.

11. The process of claim 10, further comprising recycling the fourth filtrate stream to the second crystallization stage.

12. The process of claim 11, wherein the fourth filtrate stream comprises about 70 to 80 wt. % PX based on the total weight of xylenes in the fourth filtrate stream.

13. The process of claim 12, wherein the PX product stream comprises about 99.7 wt. % PX based on the total weight of xylenes within the PX product stream.

14. A process, comprising:
(a) flowing a feed stream to a separation tower;
(b) separating a xylenes-containing stream from the feed stream within the separation tower, wherein the xylenes-containing stream comprises para-xylene (PX), meta-xylene (MX), and ortho-xylene (OX);
(c) flowing the xylenes-containing stream to a first crystallization stage;
(d) lowering a temperature of the xylenes-containing stream to −100° F. or lower within the first crystallization stage to crystallize at least some of the PX and at least some of one of both of the MX and the OX within the xylenes-containing stream;
(e) separating the xylenes-containing stream into a first crystallization effluent stream and a first filtrate stream after (d);
(f) flowing the first crystallization stage effluent stream to a second crystallization stage after (e);

(g) changing the temperature of the first crystallization stage effluent stream within the second crystallization stage to above approximately −90° F. without feeding a stream of a solvent immiscible to first crystallization stage effluent into the second crystallization stage;
(h) separating the first crystallization stage effluent stream into a second crystallization stage effluent stream and a second filtrate stream after (g);
(i) flowing the second filtrate stream to a first liquid phase isomerization unit to produce a first isomerized stream; and
(j) recycling the first isomerized stream to at least one of: the first crystallization stage; or
the second crystallization stage.

15. The process of claim 14, further comprising:
(k) flowing at least a portion of the first filtrate stream to a second liquid phase isomerization unit to produce a second isomerized stream; and
(l) recycling the second isomerized stream to the first crystallization stage.

16. The process of claim 15, further comprising:
(m) flowing at least a portion of the first filtrate stream to a vapor phase isomerization unit to produce a second isomerized stream; and
(n) recycling the second isomerized stream to the separation tower.

17. The process of claim 16, further comprising separating a $C_{7-}$ hydrocarbon-containing stream from the second isomerized stream before (l).

18. The process of claim 17, further comprising:
(o) flowing the second crystallization stage effluent stream to a third crystallization stage;
(p) changing the temperature of the second crystallization stage effluent stream within the third crystallization stage to a second point above about −54.2° F. and below 56° F.;
(q) separating from the second crystallization stage effluent stream a third crystallization stage effluent stream and a third filtrate stream after (p);
(r) flowing the third crystallization stage effluent stream to a fourth crystallization stage;
(s) changing the temperature of the third crystallization stage effluent stream with the fourth crystallization stage to a third point above the second point and below 56° F.; and
(t) separating from the third crystallization stage effluent stream a PX product stream and a fourth filtrate stream.

19. The process of claim 18, further comprising recycling the fourth filtrate stream to the second crystallization stage.

* * * * *